United States Patent
Yang et al.

(10) Patent No.: US 7,666,884 B2
(45) Date of Patent: Feb. 23, 2010

(54) N-(2-SUBSTITUTED PHENYL)-N-METHOXYCARBAMATES AND THEIR PREPARATION AND USE THEREOF

(75) Inventors: Chunhe Yang, Shenyang (CN); Liwen Geng, Shenyang (CN); Defeng Zhou, Shenyang (CN); Ling Peng, Shenyang (CN); Hong Zhang, Shenyang (CN); Dongliang Cui, Shenyang (CN); Zhinian Li, Shenyang (CN); Liangqing Wang, Shenyang (CN); Shouguo Zang, Shenyang (CN); Zeyong Zhang, Shenyang (CN)

(73) Assignee: Shenyang Research Institute of Chemical Industry, Shenyang (CN)

( * ) Notice: Subject to any disclaimer, the term of this patent is extended or adjusted under 35 U.S.C. 154(b) by 227 days.

(21) Appl. No.: 11/814,023

(22) PCT Filed: Jan. 25, 2006

(86) PCT No.: PCT/CN2006/000150

§ 371 (c)(1),
(2), (4) Date: Jul. 16, 2007

(87) PCT Pub. No.: WO2006/081759

PCT Pub. Date: Aug. 10, 2006

(65) Prior Publication Data

US 2009/0048309 A1    Feb. 19, 2009

(30) Foreign Application Priority Data

Feb. 6, 2005    (CN) .................. 2005 1 0045856

(51) Int. Cl.
*A61K 31/44* (2006.01)
*C07D 213/64* (2006.01)
(52) U.S. Cl. ............... 514/346; 514/349; 514/350; 546/291; 546/309; 546/314

(58) Field of Classification Search ............... None
See application file for complete search history.

(56) References Cited

U.S. PATENT DOCUMENTS 5,824,705 A    10/1998    Mueller et al.

FOREIGN PATENT DOCUMENTS

| JP | 7-278090 | 10/1995 |
| JP | 2001-55304 | 2/2001 |

*Primary Examiner*—Zinna N Davis
(74) *Attorney, Agent, or Firm*—Smith, Gambrell & Russell, LLP

(57) ABSTRACT

The present invention belongs to the field of agricultural fungicide and in particular disclosed N-(2-substituted phenyl)-N-methoxycarbamates and their preparation as well as use. Compounds according to the present invention are shown as the general formula I.

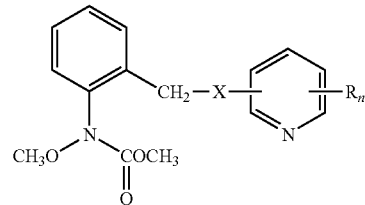

Compounds according to the present invention have very good fungicidal activities and can be used for the control of plant fungicidal diseases, such as wheat powdery mildew, melon powdery mildew, apple powdery mildew, grape powdery mildew, strawberry powdery mildew, wheat rust, soybean rust, wheat Pythium root rot, cucumber Alternaria blight, rice "bakanae" disease, rice sheath blight, cucumber Fusarium wilt, cucumber anthracnose, rice blast, rice false smut, corn southern leaf blight.

8 Claims, No Drawings

N-(2-SUBSTITUTED PHENYL)-N-METHOXYCARBAMATES AND THEIR PREPARATION AND USE THEREOF

This application is a 371 National Phase application of International Application Serial No. PCT/CN2006/000150, filed 26 Jan. 2006, and claims the benefit of CN 200510045856.1, filed 6 Feb. 2005.

FIELD OF THE INVENTION

The present invention belongs to the field of agricultural fungicide, relates to certain N-(2-substituted phenyl)-N-methoxycarbamates and their preparation and use thereof

BACKGROUND OF THE INVENTION

WO-93/15046 discloses carbamates of the following formula for protecting crop:

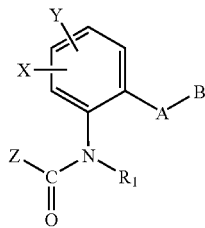

WO-96/01256 discloses 2-[(dihydro)pyrazol-3'-yloxymethylene]anilides of the following formula for controlling animal pests and harmful fungi:

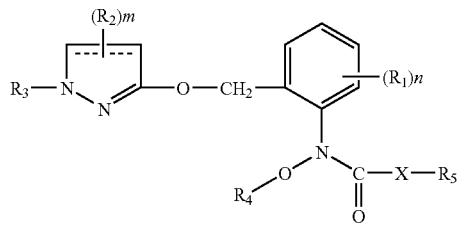

But the carbamates included in the present invention are not reported.

SUMMARY OF THE INVENTION

The object of the present invention is to disclose certain N-(2-substituted phenyl)-N-methoxycarbamates which can control harmful fungi of crop in lower dose.

The technical scheme of the present invention is as follows:

The present invention provides N-(2-substituted phenyl)-N-methoxycarbamates with the following formula I:

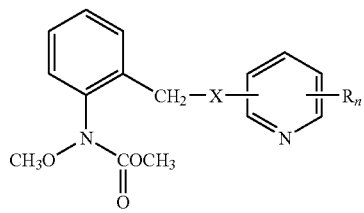

Where the substituents in the formula I have the following meaning:

X is selected from O, S, COO or $NR^a$; $R^a$ is selected from hydrogen, $C_1$-$C_3$ alkyl, $C_2$-$C_4$alkenyl or $C_2$-$C_4$alkynyl;

n is 1-4; R is selected from halogen or amido, if n>1, R may be same or different.

And their salts.

$R_n$ in the formula I above means the number of substituent R on the pyridine ring is n; Halogen are fluorine, chlorine, bromine or iodine.

In particular, preferred compound in this case is which in the formula I, X is selected from O or $NR^a$; $R^a$ is hydrogen, $C_1$-$C_3$ alkyl, $C_2$-$C_4$alkenyl or $C_2$-$C_4$alkynyl; R is selected from 1-4 halogen atom(s), which is(are) same or different and selected from fluorine, chlorine or bromine respectively.

Further preferred compound in this case is which in the formula I, X is O; R is selected from 1-4 halogen atom(s), which is(are) same or different and selected from fluorine or chlorine respectively.

More further preferred compound in this case is which in the formula I, X is O and situated at o-position of nitrogen on the pyridine ring; R is selected from 1-4 halogen atom(s), which is(are) same or different and selected from fluorine or chlorine respectively.

The present invention can be explained by the compounds in table 1, but is not limited by them.

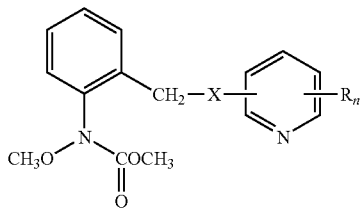

TABLE 1

| NO. | X(position of X) | $R_n$ | MP(° C.) |
|---|---|---|---|
| 1 | O(2-) | 3-Cl | |
| 2 | O(2-) | 4-Cl | |
| 3 | O(2-) | 5-Cl | |
| 4 | O(2-) | 6-Cl | |
| 5 | O(2-) | 3,4-Cl2 | |
| 6 | O(2-) | 3,5-Cl2 | oil |
| 7 | O(2-) | 3,6-Cl2 | 86-87° C. |
| 8 | O(2-) | 4,5-Cl2 | |
| 9 | O(2-) | 4,6-Cl2 | |
| 10 | O(2-) | 5,6-Cl2 | 66-68° C. |
| 11 | O(2-) | 3,4,5-Cl3 | |
| 12 | O(2-) | 3,4,6-Cl3 | |
| 13 | O(2-) | 3,5,6-Cl3 | 94-95° C. |
| 14 | O(2-) | 4,5,6-Cl3 | |
| 15 | O(2-) | 3,4,5,6-Cl4 | 87-88° C. |
| 16 | O(2-) | 3-Cl, 4-F | |
| 17 | O(2-) | 5-Cl, 3-F | oil |
| 18 | O(2-) | 3-Cl, 6-F | |
| 19 | O(2-) | 4-Cl, 3-F | |
| 20 | O(2-) | 4-Cl, 5-F | |
| 21 | O(2-) | 4-Cl, 6-F | |
| 22 | O(2-) | 5-Cl, 3-F | |
| 23 | O(2-) | 5-Cl, 4-F | |
| 24 | O(2-) | 5-Cl, 6-F | |
| 25 | O(2-) | 5-Cl, 3,4-F2 | |
| 26 | O(2-) | 6-Cl, 3-F | |
| 27 | O(2-) | 6-Cl, 4-F | |
| 28 | O(2-) | 6-Cl, 5-F | |
| 29 | O(2-) | 6-Cl, 3,4-F2 | |
| 30 | O(2-) | 6-Cl, 3,5-F2 | |
| 31 | O(2-) | 6-Cl, 4,5-F2 | |
| 32 | O(2-) | 3,5-Cl2, 6-F, 4-NH2 | 120-121° C. |

TABLE 1-continued

| NO. | X(position of X) | $R_n$ | MP(° C.) |
|---|---|---|---|
| 33 | O(2-) | 3-F | |
| 34 | O(2-) | 4-F | |
| 35 | O(2-) | 5-F | |
| 36 | O(2-) | 6-F | |
| 37 | O(2-) | 3,4-F2 | |
| 38 | O(2-) | 3,5-F2 | |
| 39 | O(2-) | 3,6-F2 | |
| 40 | O(2-) | 4,5-F2 | |
| 41 | O(2-) | 4,6-F2 | |
| 42 | O(2-) | 5,6-F2 | |
| 43 | O(2-) | 3,4,5-F3 | |
| 44 | O(2-) | 3,4,6-F3 | |
| 45 | O(2-) | 4,5,6-F3 | |
| 46 | O(2-) | 3,5,6-F3 | |
| 47 | O(2-) | 3,4,5,6-F4 | |
| 48 | O(3-) | 6-Cl | oil |
| 49 | NH(4-) | 3,5-Cl2, 2,6-F2 | 82-83° C. |
| 50 | NH(2-) | 5-I | oil |
| 51 | NH(3-) | 6-Cl | oil |
| 52 | COO(3-) | 2-Cl | oil |
| 53 | COO(3-) | 6-Cl | oil |

The present invention also includes some methods of preparing N-(2-substituted phenyl)-N-methoxycarbamates shown in the formula I: through reacting compound III with compound II in the presence of a base, compound I can be obtained. The reaction equation is as follows:

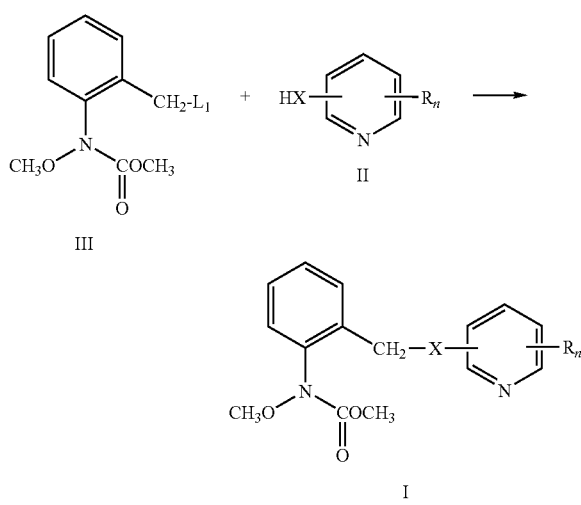

$L_1$ is a nucleophilically replaceable group: for example halogen (eg. fluorine, chlorine, bromine, or iodine); or sulfonate (eg. methylsulfante, trifluoromethylsulfate, phenylsulfate, 4-methylphenylsulfate).

X, n and R are the same as above.

Reaction is often carried out in organic solvent, the dosage of solvent is 100-3000 ml/(mol starting material).

Suitable solvents are aromatic hydrocarbons such as toluene, xylene, halogenated hydrocarbons such as methylene chloride, chloroform, chlorobenzene, ethers such as diethyl ether, tert-butyl methyl ether, dioxane, tetrohydrofuran, nitrile such as acetonitrile, propionitrile, alcohols such as methanol, ethanol, n-propanol, i-propanol, n-butanol, tert-butanol, ketones such as acetone, methyl ethyl ketone, and dimethyl sulfoxide, dimethylformamide, dimethylacetomide, preferably dimethylformamide, methylene chloride, acetone, toluene or tert-butyl methyl ether. Mixtures of above-mentioned solvents can also be used.

Suitable reaction temperature is from –20° C. to boiling point of solvent. Preferable reaction temperature is from 0° C.-100° C.

Suitable reaction time is from 0.5-48 hours.

Suitable bases are alkali metal or alkaline earth metal hydroxides (eg. lithium hydroxide, sodium hydroxide, potassium hydroxide or calcium hydroxide), alkali metal or alkaline earth metal oxides (eg. lithium oxide, sodium oxide, calcium oxide or magnesium oxide), alkali metal or alkaline earth metal hydride (eg. lithium hydride, sodium hydride, potassium hydride or calcium hydride), alkali metal amides (eg. lithium amide, sodium amide or potassium amide), alkali metal or alkaline earth metal carbonates (eg. lithium carbonate, sodium carbonate, potassium carbonate or calcium carbonate), alkali metal hydrogen carbonates (eg. sodium hydrogen carbonate), alkali metal alkyls (eg. methyllithium, butyllithium or phenyllithium), alkylmagnesium halides (eg. methylmagnesium chloride), alkali metal or alkaline earth metal alkoxides (eg. sodium methoxide, sodium ethoxide, potassium ethoxide, potassium tert-butoxide or dimethoxymagnesium), organic bases (eg. trimethylamine, triethylamine, triisopropylethylamine, N-methylpiperidine, pyridine or substituted pyridines).

Sodium hydroxide, potassium hydroxide, sodium carbonate or potassium carbonate are particularly preferred.

The bases are in general used in an equimolar amount, in an excess or if appropriate as a solvent.

It may be advantageous for the reaction first to convert compound II to the corresponding metal compound by using the base and then to react it with the compound III.

Compound III can be prepared by the known methods (re. described in WO9315046, WO0246142, U.S. Pat. No. 5,824,705).

Compound II can be purchased, and also be prepared from the corresponding halogenated pyridine by the known methods such as hydrolysis or ammonolysis (re. J. Chem. Soc. 1971, 167, JP58154561).

Compound I also can be prepared according to the reaction equation below:

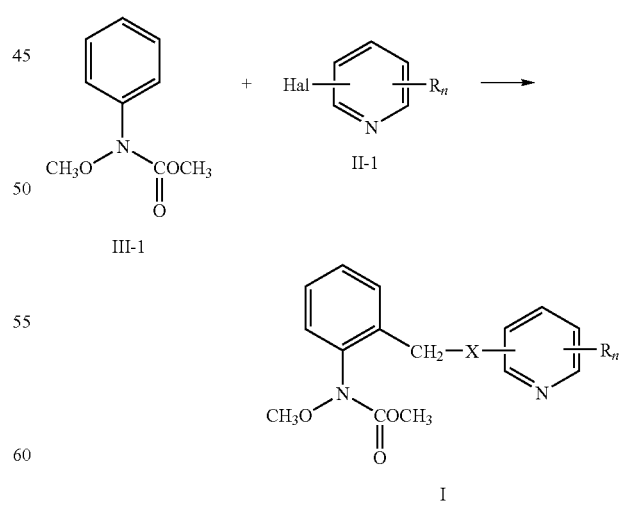

Hal is a halogen atom in formula II-1, other substituents here are the same as the above.

The present invention contains the salts of N-(2-substituted Phenyl)-N-methoxycarbamates of the formula I.

Acids for preparing the above-mentioned salts are, inorganic acids (eg. hydrohalic acid such as hydrochloric or hydrobromic acid, phosphoric acid, sulfuric acid, nitric acid), or organic acids (eg. formic acid, acetic acid, oxalic acid, malonic acid, lactic acid, malic acid, amber acid, tartaric acid, citric acid, salicylic acid, p-toluenesulfonic acid, dodecylbenzenesulfonic acid).

The N-(2-substituted Phenyl)-N-methoxycarbamates and their salts have excellent fungicidal activities in this case, and can be used for the control of all kinds of crop diseases caused by the pathogens of Zygomycotina, Ascomycotina, Basidiomycotina and Deuleromcotina.

The present invention also contains a composition suitable for controlling harmful fungi, including active compound of the general formula I from 0.1 to 99% by weight and carriers acceptable in agriculture.

The above-mentioned active composition can be a compound or a mixture of some compounds of formula I.

In the present invention, the carriers of the composition are the substances that meet undermentioned conditions: after it is mixed up with active compound, expediently to be used for the objects, for example: plants, seeds or soil; or advantageously to be reserved, transported or operated. Carriers can be solid or liquid etc, that usually is used in formulation.

Suitable solid carriers are natural or synthetical silicate (eg. diatomite, steatite, aluminium silicate(kaolin), Montmorillonite or mica); calcium carbonate, calcium sulfate, ammonium sulfate; synthetical calcium oxysilicate or aluminium silicate; elements (eg. carbon or sulfur); natural or synthetical resin (benzofuran, PVC, styrene polymer or copolymer); solid polychlorophenol; wax (eg. beeswax, olefin).

Suitable liquid carriers are water; alcohol (e.g. i-propanol, ethanol, n-butanol, glycerol or glycol; ketone (e.g. acetone, methyl ethyl ketone, methyl isobutyl ketone, pyrrolidinone, hypnone or cyclohexone); ethers; aromatic hydrocarbons (e.g. toluene, xylene or solvent oil); petroleum fraction (e.g. kerosene or mineral oil); vegetable oil; dimethylformamide etc. The mixture of these liquids are often suitable.

It is convenient for transportation and being used usually to prepare the composition into formulation(s), which is(are) diluted by user before using. A few of surfactant helps to dilution. Thus, the composition in the present invention usually contains not less than a kind of surfactant.

Surfactants may be emulsifiers, dispersants, infiltrating agents, adhesives or wetting agents, and may be ionic surfactants or nonionic surfactants. For example: high-level fatty acids and their salts including not less than 8 carbons; salts of sulfonic acid, eg. alkylbenzene sulfonate, alkyl sulfonates, ethyl fatty acid ester sulfonates, secondary alcohol polyoxyethylene ether succinate suifonates, butyl naphthalene sulfonates, fatty acid amide sulfonates; sulfates, eg. fatty alcohol sulfates, fatty alcohol polyoxyethylene ether sodium suifates; oleoyl amino acid sodium, lauroyl creatin sodium of the condensation products of fatty acid acyl chloride and protein hydrolysate; phosphates; alkylamine salt type cation surfactants in amine salt type cation surfactants; amino alcohol fatty acid derivative cation surfactants; glycin-type surfactants in amino acid-type amphoteric surfactants; imidazolin-type amphoteric surfactants; long-chain fatty alcohol polyoxyethlene ethers, alkyl acid polyoxyethlene ethers, polyoxyethlene alkyl alcohol acylamines in polyglycol-type nonionic surfactants; glycerin fatty acids and pentacrythritol fatty acid ester in polyol-type nonionic surfactants, sorbitol fatty acid ester, anhydrosorbitol fatty acid and polyoxyethlene anhydrosorbitol fatty acid ester; alkylthioalcohol polyoxyethlene ether; crylic acid copolymer in macromolecule surfactants; silica surfactants etc.

The compositions of the present invention can be manufactured to all kinds of formulations according to the declared methods, such as AS(Aqueous Solution), WP(Wettable Powder), DP(Dustable Powder), GR(Granule), CE(Concentrated Emulsion), EC(Emulsifiable Concentrate), WG(Water Dispersible Granules), SC(Suspension concentrate), AE(Aerosol Dispenser) or FO(Smoke Fog) etc.

The compositions in the present invention can be applied in an effective dosage for the control of different diseases on various crops by foliar spray, seed treatment or soil treatment.

For some cases, one or more other fungicides can be applied along with the compounds in this invention, and additional advantages and efficacies can be achieved.

The compositions in the present invention can be used alone or along with other known insecticides, herbicides, plant growth regulators or fertilizers.

The compounds and compositions in the present invention have excellent fungicidal activities and can be applied for the control of the diseases caused by the pathogens of Zygomycotina, Ascomycotina, Basidiomycotina and Deuleromcotina, including, but not confined by the following plant diseases: wheat powdery mildew, melon powdery mildews, apple powdery mildew, grape powdery mildew, strawberry powdery mildew; wheat rust, soybean rust, wheat root rot, cucumber scab, rice bakanae disease, rice sheath blight, cucumber wilt blight, cucumber anthracnose, rice blast, rice false smut and corn curvalaria leaf spot.

Therefore the compounds and compositions in the present invention can be used as agricultural fungicide for the control of diseases on wheat, cucumber, watermelon, apples, grapes, strawberry, soybean, rice and maize etc.

It must be explained that in the range limited by the claims of the present invention, all kinds of counterchange and change can be done.

DESCRIPTION OF THE INVENTION IN DETAIL

The following examples are the representative ones in the present invention, but they do not limit the present invention.

SYNTHESIS EXAMPLES

Example 1

Preparation of Methyl N-methoxy-N-(2-((3,5,6-trichloropyridin-2-yl)oxymethyl) phenyl)carbamate (compound 13)

Equation:

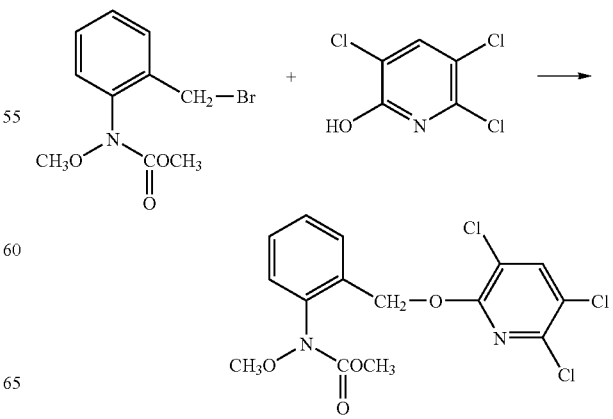

0.4 g (2 mmol) 3,5,6-trichloropyridinol (purchased) and 0.6 g (2.2 mmol) N-(2-bromomethyl phenyl)-N-methoxycarbamate (prepared according to WO02/46142) are dissolved into 5 ml DMF, then 0.45 g potassium carbonate is added into them, the mixture keeps being stirred and reacting at room temperature for 6 hours.

The reaction solution is absorbed by ethyl acetate, washed by water, after washed by saturated brine again and dried by anhydrous sodium sulfate, distill the solvent out in vacuo. Separating through silica gel column, 0.55 g pale yellow solid obtained, as compound 13. Content: 95%, MP: 94-95° C.

Example 2

Preparation of Methyl N-(2-((3,5-dichloro-2,6-difluoropyridin-4-yl)aminomethyl) phenyl)-N-methoxycarbamate (compound 49)

Equation:

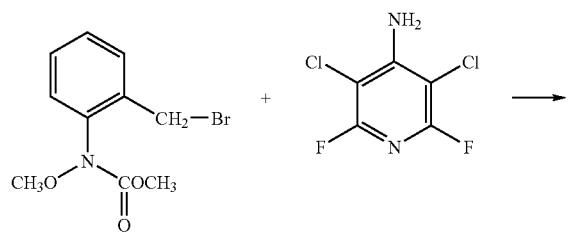

-continued

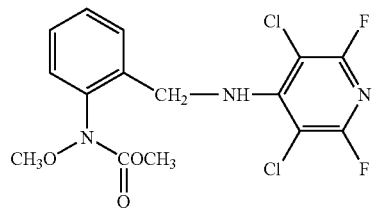

0.43 g (2.5 mmol) 4-amino-3,5-dichloro-2,6-difluoro-pyridine and 0.77 g (2.8 mmol) N-(2-bromomethyl phenyl)-N-methoxycarbamate are dissolved into 5 ml DMF, then 1.0 g potassium carbonate is added into them, the mixture keeps being stirred and reacting at 30-35° C. for 4 hours.

The reaction solution is absorbed by ethyl acetate, washed by water, after washed by saturated brine again and dried by anhydrous sodium sulfate, distill the solvent out in vacuo. Separating through silica gel column, 0.6 g pale yellow solid obtained, as compound 49. Content: 95%, MP: 82-83° C.

According to the above mentioned methods, the rest compounds in formula I can be obtained through suitably changing starting compound.

The NMR ($^1$HNMR, 300 MHz, internal reference: TMS, solvent: $CDCl_3$) datum of some compounds are in table 2.

TABLE 2

| NO. | Structure | $^1$HNMR |
|---|---|---|
| 6 | 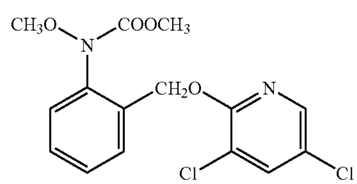 | 3.77 (s, 3H), 3.81 (s, 3H), 5.20 (s, 2H), 7.29-7.35 (m, 2H) 7.38-7.40 (m, 3H), 7.53-7.54 (m, 1H). |
| 7 | 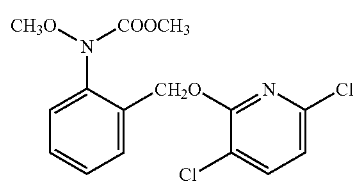 | 3.79 (s, 3H), 3.80 (s, 3H), 5.49 (s, 2H), 6.84 (d, 1H), 7.55 (d, 1H), 7.34-7.40 (m, 3H), 7.62-7.46 (m, 1H) |
| 10 | 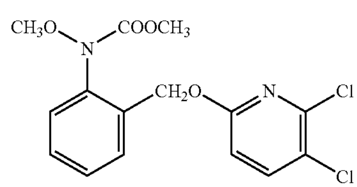 | 3.77 (s, 3H), 3.78 (s, 3H), 5.40 (s, 2H), 6.68 (d, 1H), 7.33-7.39 (m, 3H), 7.52-7.54 (m, 1H), 7.59 (d, 1H) |
| 13 | 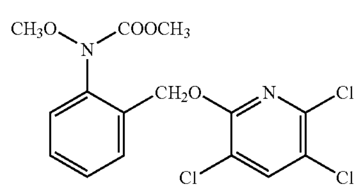 | 3.79 (s, 3H), 3.81 (s, 3H), 5.48 (s, 2H), 7.36-7.40 (m, 3H), 7.60 (m, 1H), 7.72 (s, 1H) |

TABLE 2-continued

| NO. | Structure | ¹HNMR |
|---|---|---|
| 15 | 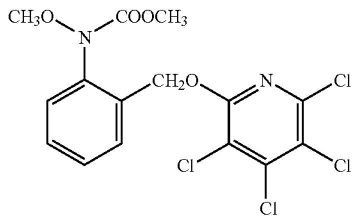 | 3.79 (s, 3H), 3.82 (s, 3H), 5.49 (s, 2H), 7.27-7.40 (m, 3H), 7.59 (m, 1H). |
| 17 | 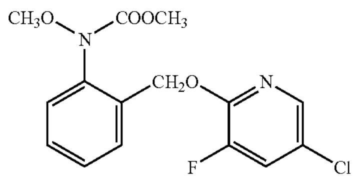 | 3.78 (s, 3H), 3.82 (s, 3H), 5.20 (s, 2H), 7.11-7.15 (m, 1H) 7.24-7.25 (m, 2H) 7.36-7.40 (m, 3H). |
| 32 | 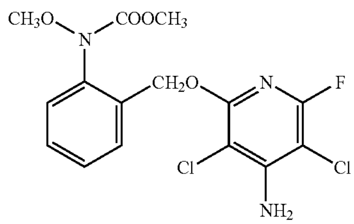 | 3.79 (s, 3H), 3.81 (s, 3H), 5.13 (b, 2H), 5.40 (s, 2H), 7.34-7.38 (m, 3H), 7.59 (m, 1H) |
| 48 | 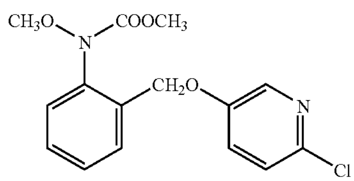 | 3.74 (s, 3H), 3.81 (s, 3H), 5.15 (s, 2H), 7.22-7.23 (m, 2H), 7.40 (m, 4H), 8.10 (d, 1H). |
| 49 | 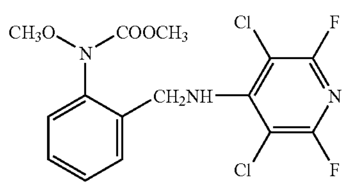 | 3.79 (s, 3H), 3.81 (s, 3H), 5.75 (bt, 1H), 5.4 (d, 2H), 7.34-7.38 (m, 3H), 7.62-7.64 (m, 1H) |
| 50 | 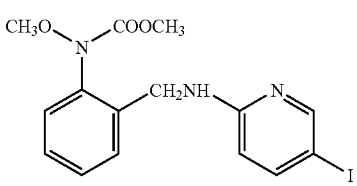 | 3.74-3.80 (s, 6H), 4.50-4.52 (d, 2H), 5.30-5.43 (d, 1H) 6.20-6.22 (d, 1H), 7.32-7.34 (m, 3H), 7.45-7.46 (m, 1H) 7.54-7.59 (m, 1H), 8.20 (s, 1H). |
| 51 | 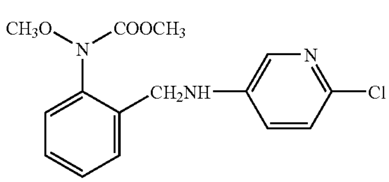 | 3.98 (s, 6H), 4.75 (s, 2H), 7.10-7.20 (m, 2H), 7.24-7.28 (m, 1H), 7.35-7.36(m,2H),7.74-7.78 (t, 1H), 8.42 (d, 1H). |
| 52 | 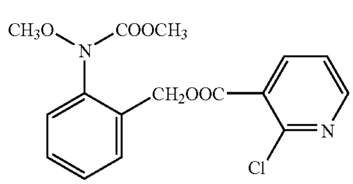 | 3.76 (s, 6H), 5.46 (s, 2H), 7.32-7.36 (m, 3H), 7.40-7.41 (m, 3H), 7.58-7.62 (m, 1H), 8.21-8.24 (m, 1H). |

TABLE 2-continued

| NO. | Structure | ¹HNMR |
|---|---|---|
| 53 | 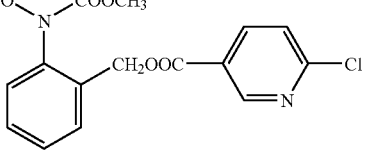 | 3.77 (s, 6H), 5.45 (s, 2H), 7.38-7.42 (m, 3H), 7.44 (s, 1H), 7.53-7.56 (m, 1H), 8.27 (q, 1H), 9.01 (d, 1H) |

FORMULATION EXAMPLES

All the components are calculated according to weight percent, and active component is added according to the percent of pure active compound.

Example 3

60% WP

| | |
|---|---|
| Compound 13 | 60% |
| Sodium dodecylbenzenesulfonate | 1% |
| Sodium ligninsulfonate | 6% |
| Diffusing agent NNO | 5% |
| Diatomite | added to 100% |

All the above mentioned components (all solid) are mixed up and crushed in muller, until the granularity of the mixture accords with the Criterion ($\leqq 44$ μm), then 60% WP obtained.

Example 4

50% WG

| | |
|---|---|
| Compound 13 | 50% |
| Anhydrosorbitol sulfonate | 1% |
| Polyethylene pyrrolidinone | 3% |
| Sodium ligninsulfonate | 10% |
| Diatomite | added to 100% |

All the above mentioned components are mixed up and crushed in muller, and then mixed with some water, granulated and dried, then obtain 50% WG.

Example 5

15% EC

| | |
|---|---|
| Compound 13 | 15% |
| Pyrrolidinone | 10% |
| Styrenylphenolpolyoxyethlene ether (emulsificating agent A) | 7% |
| Calcium dodecylbenzenesulfonate (emulsificating agent B) | 5% |
| Solvent oil | added to 100% |

Compound 13 is dissolved into Pyrrolidinone and solvent oil, then add emulsificating agent A and B, and mix them up to clear homogeneous solution, then 15% EC obtained.

Example 6

35% EC

| | |
|---|---|
| Compound 49 | 35% |
| Cyclohexanone | 20% |
| emulsificating agent OP-10 (emulsificating agent A) | 7% |
| Sodium dodecylbenzenesulfonate (emulsificating agent B) | 5% |
| Solvent oil | added to 100% |

Compound 49 is dissolved into Cyclohexanone and Solvent oil, then add emulsificating agent A and B, and mix them up to clear homogeneous solution, then 35% EC obtained.

BIOACTIVITY TEST EXAMPLES

Example 7

Fungicidal Activity Tests Against Wheat Powdery Mildew

Compounds for test were weighed quantitatively and dissolved into acetone of suitable volume (acetone's volume is 10% of the whole solution's volume), then diluted by water containing 0.1% (volume percent, the same below) Tween 80, into 200 mg/L. By turntable crop sprayer, wheat seedlings with 1 leaf and 1 core were treated under the spray pressure of 1.5 kg/cm² and the spray volume of about 1000 L/hm², then naturally dry, 24 hours later wheat powdery mildew spore was inoculated, and then continue being incubated in greenhouse. Assessment of efficacy was carried out by visual observation 7 days later after treatment. Fungicidal activity test results of part compounds of formula I were listed in Table 3.

TABLE 3

| Compound# | Control(%) |
|---|---|
| 6 | 60 |
| 7 | 100 |
| 10 | 100 |
| 13 | 100 |
| 15 | 100 |
| 32 | 60 |
| 49 | 85 |

Example 8

Protective Activity Test Against Wheat Powdery Mildew

Compounds for test were weighed quantitatively and dissolved into acetone of suitable volume (acetone's volume is 10% of the whole solution's volume), then diluted with water containing 0.1% Tween 80 into the medicament solution at the needed concentration, and then diluted with the same water into a series of concentration for test. By turntable crop sprayer, wheat seedlings with 1 leaf and 1 core were treated under the spray pressure of 1.5 kg/cm$^2$ and the spray volume of about 1000 L/hm$^2$, then naturally dry, inoculated 24 hours later. First, spray clear water onto wheat seedlings by sprayer, until the leaves were wet. And then wheat powdery mildew spores were shaken off onto the leaves of the wheat, continue being incubated in greenhouse. Assessment of efficacy was carried out by visual observation compared with blank comparison 7 days later. Kresoxim-methyl as standard chemical (BAS490F, preparation according to U.S. Pat. No. 5,354,883, content 95%) was tested with the same method and at the same concentration. Test results were listed in Table 4.

TABLE 4

| compound | concentration mg/L control % | | | | |
|---|---|---|---|---|---|
| | 12.5 | 6.25 | 3.125 | 1.56 | 0.78 |
| 7 | 100 | 100 | 100 | 60 | 30 |
| 10 | 100 | 100 | 100 | 75 | 50 |
| 13 | 100 | 100 | 100 | 100 | 100 |
| 15 | 100 | 60 | 40 | 15 | — |
| Kresoxim-methyl | 100 | 98 | 70 | 40 | 15 |
| Untreated | 0 | | | | |

Results shown that the preventative activities of the tested compound 7, 10, 13 are obviously better than the one of the standard chemical.

Example 9

Curative Activity Test Against Wheat Powdery Mildew

Compound 13 (content 95%) was weighed quantitatively and dissolved into acetone of suitable volume (acetone's volume is 10% of the whole solution's volume), then diluted with water containing 0.1% Tween 80 into the solution of the medicament at the needed concentration. Spray clear water onto wheat seedlings with 1 leaf and 1 core by sprayer, until the leaves were wet. And then wheat powdery mildew spores, which had been incubated for 7 days, were shaken off onto the leaves of the wheat, then continue being incubated in greenhouse for 4 days. By turntable crop sprayer, wheat seedlings with 1 leaf and 1 core were treated under the spray pressure of 1.5 kg/cm$^2$ and the spray volume of about 1000 L/hm$^2$, then naturally dry, and then placed in green house in normal management. Assessment of efficacy was carried out by visual observation compared with blank comparison 7 days later. Standard chemical kresoxim-methyl (BAS490F, preparation according to U.S. Pat. No. 5,354,883, content 95%) was tested with the same method and at the same concentration. Test results were listed in Table 5.

TABLE 5

| compound | concentration mg/L control % | | | | |
|---|---|---|---|---|---|
| | 12.5 | 6.25 | 3.125 | 1.56 | 0.78 |
| 13 | 100 | 100 | 70 | 35 | 10 |
| Kresoxim-methyl | 100 | 75 | 15 | 10 | 0 |
| Untreated | | | 0 | | |

Results shown that compound 13 has an excellent curative activity against wheat powdery mildew, which curative activity is 70% at 3.125 mg/L and better than the one of standard chemical.

Example 10

In Vitro Fungicidal Activity Test

PDA mycelium growth inhibition method was used for this test. Compound 13 (content 95%) was weighed quantitatively and dissolved in acetone of suitable volume (acetone's volume is 10% of the whole solution's volume), then diluted with water containing 0.1% Tween 80 into the solution of the medicament at the needed concentration, and then diluted with the same water into a series of concentration for tests. The medicament for test diluted by water was added quantitatively into the heating full-nutrition culture medium, to form culture medium including the medicament at a series of concentration, and then poured into 9-cm culture dish, after cooling, inoculated with the pathogen cake (diameter 0.5 cm) for test which was incubated in vitro, each treatment was repeated tree times. After treatment, placed in growth chamber in 27° C., 3-4 days later, observe the growth of the blank contrast fungi colony, the diameter of fungi colony was investigated and measured, and corrected inhibition ratio was calculated. Test results were listed in table 6.

TABLE 6

| | Effect of mycelium growth inhibition (%) | | | | | | | | |
|---|---|---|---|---|---|---|---|---|---|
| Concentration mg/L | Rice sheath blight | Wheat root rot | Wheat Fusarium Head Blight | Cucumber scab | Cucumber wilt blight | Cucumber anthracnose | Rice blast | Rice false smut | corn *curvalaria* leaf spot |
| 10 | 78.6 | 61.1 | 42.9 | 65.0 | 51.4 | 72.4 | 77.2 | 79.2 | 70.2 |
| 1 | 59.2 | 46.3 | 21.1 | 50.0 | 33.6 | 62.8 | 62.6 | 42.8 | 56.2 |
| 0.1 | 42.7 | 32.6 | 20.3 | 28.7 | 27.1 | 42.8 | 36.6 | 19.5 | 55.4 |

Results shown that compound 13 has fungicidal activity against various pathogens, which activity, especially against rice sheath blight, wheat root rot, Cucumber scab, cucumber anthracnose, rice blast, rice false smut and corn curvalaria leaf spot and so on, is outstanding.

Example 11

Field Test For The Control of Muskmelon Powdery Mildew (*Sphaerotheca fuliginea*)

15% EC of compound 13 was tested at the dosage of 50, 75 and 100 g a.i/hm². 50% DF of kresoxim-methyl (BASF) was standard chemical and its dosage was 75 g a.i/hm². Water treatment was set as blank comparison in addition, 5 treatments were randomly tested for 4 times respectively. The medicament was sprayed with "GONGNONG 16" manual sprayer for 4 times, at intervals of 7 days, in the dosage of 1000 L/hm². Six days after the fourth treatment assessment was carried out according to the Chinese national standard of pesticide field test protocols. Field test results showed that 15% EC of compound 13 has excellent control efficacy against muskmelon powdery mildew (*Sphaerotheca fuliginea*), which efficacy was a little better than standard chemical kresoxim-methyl 50% DF in the dosage of 50~100 g a.i./hm², showed in table 7.

TABLE 7

| Treatment | Rate (g a · i/hm²) | Disease severity (%) | Control (%) |
|---|---|---|---|
| Compound 13 15% EC | 50 | 5.056 | 92.97 |
| | 75 | 1.556 | 97.84 |
| | 100 | 0.778 | 98.92 |
| Kresoxim-methyl 50% DF | 75 | 4.361 | 93.94 |
| CK | | 71.959 | — |

The invention claimed is:

1. An N-(2-substituted phenyl)-N-methoxycarbamate having formula I:

Where the substituents in the formula I have the following meaning:
X is O, S, COO or $NR^a$; $R^a$ is selected from hydrogen, $C_1$-$C_3$ alkyl, $C_2$-$C_4$ alkenyl or $C_2$-$C_4$ alkynyl;
n is 1-4;
R is selected from halogen or amido respectively, if n>1, R may be same or different;
or their salt.

2. The N-(2-substituted phenyl)-N-methoxycarbamate according to claim 1, wherein:
X is selected from O or $NR^a$, $R^a$ is hydrogen, $C_1$-$C_3$ alkyl, $C_2$-$C_4$ alkenyl or $C_2$-$C_4$ alkynyl; and
R is selected from 1-4 halogen atom(s), which is (are) same or different and selected from fluorine, chlorine or bromine respectively.

3. The N-(2-substituted phenyl)-N-methoxycarbamate according to claim 2, wherein:
X is O; and
R is selected from 1-4 halogen atom(s), which is(are) same or different and selected from fluorine or chlorine respectively.

4. The N-(2-substituted phenyl)-N-methoxycarbamate according to claim 3, wherein:
X is O and situated at o-position of nitrogen on the pyridine ring; and
R is selected from 1-4 halogen atom(s), which is (are) same or different and selected from fluorine or chlorine respectively.

5. A process for preparing the N-(2-substituted phenyl)-N-methoxycarbamate according to claim 1, which comprises reacting a compound having formula III with a compound having the formula II in the presence of a base; the reaction equation is as follows:

wherein $L_1$ is a nucleophilically replaceable group;
X is O, S, COO or $NR^a$; $R^a$ is selected from hydrogen, $C_1$-$C_3$ alkyl, $C_2$-$C_4$ alkenyl or $C_2$-$C_4$ alkynyl;
R may be same or different and selected from halogen or amido; and
n is 1-4.

6. A method for controlling fungi in a crop which comprises administering to the crop the N-(2-substituted phenyl)-N-methoxycarbamate-according to claim 1.

7. A fungicidal composition, comprising the compound of claim 1 is as an active ingredient, wherein the weight percentage of the active ingredient in the composition is from 0.10% to 99%.

8. A method for controlling fungi in a crop which comprises administering to the crop the composition according to claim 7.

* * * * *